Figure 1:
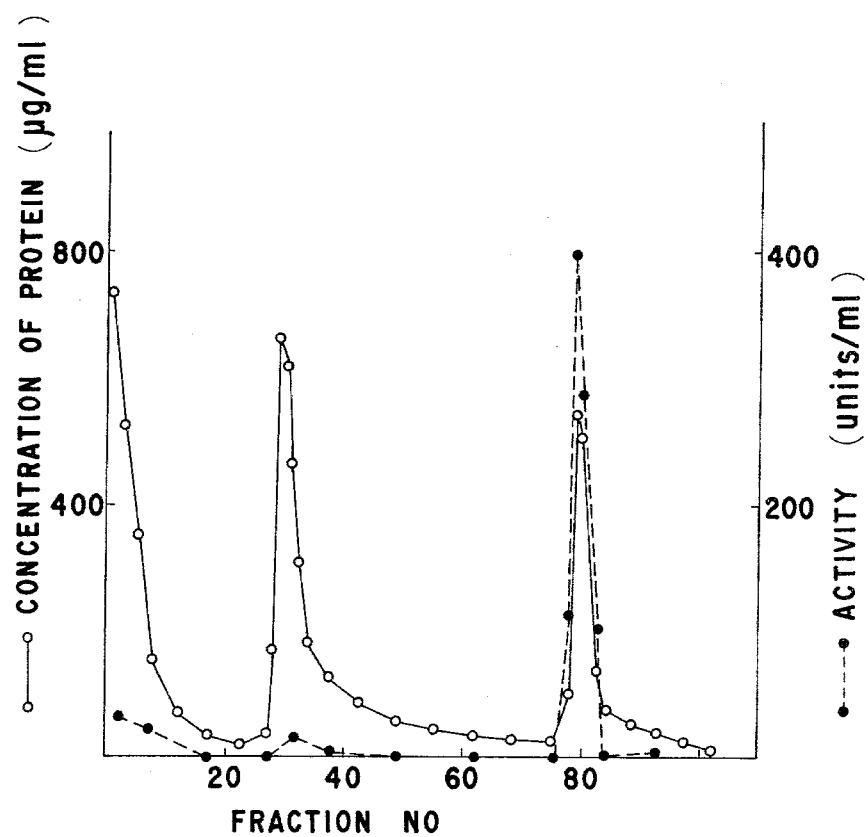

United States Patent [19]

Kanbayashi et al.

[11] 4,234,570

[45] Nov. 18, 1980

[54] PROTEINIC ACTIVE SUBSTANCES

[75] Inventors: Yoshinori Kanbayashi, Ohtsu; Michio Ui, Sapporo; Koichi Hosoda, Shiga; Akira Ito; Shigeki Kurokawa, both of Ohtsu; Akio Terashima, Shiga; Isamu Takahashi, Ohtsu; Motoyuki Yajima, Ohtsu; Chikanori Tomioka, Ohtsu; Tsutomu Nakamura, Ohtsu; Katsumi Nogimori, Kyoto; Taira Okamoto, Kusatsu, all of Japan

[73] Assignee: Kakenyaku Kako Kabushiki Kaisha, Tokyo, Japan

[21] Appl. No.: 911,665

[22] Filed: Jun. 1, 1978

[30] Foreign Application Priority Data

Jun. 10, 1977 [JP] Japan .................................. 52-69154

[51] Int. Cl.³ .................... A61K 37/00; C07C 103/52; C12P 21/00

[52] U.S. Cl. ........................................ 424/177; 435/68; 260/112 R

[58] Field of Search ................... 424/177; 260/112 R; 435/68

[56] References Cited

PUBLICATIONS

Katada et al., Biological Abstract 66, 1978, p. 38918.
R. Parton et al., Chem. Abst. 83, (1975), 4600g.
Takahiko Sumi et al., Endocrinology 97, 352–358, (1975).

*Primary Examiner*—Delbert R. Phillips
*Attorney, Agent, or Firm*—Stevens, Davis, Miller & Mosher

[57] ABSTRACT

Novel biologically active substances prepared by dissociating the protein obtained from the cultivation of the microorganism Bordetella and having insulin secretion promoting action as well as glucose tolerance improving action for mammals.

14 Claims, 12 Drawing Figures

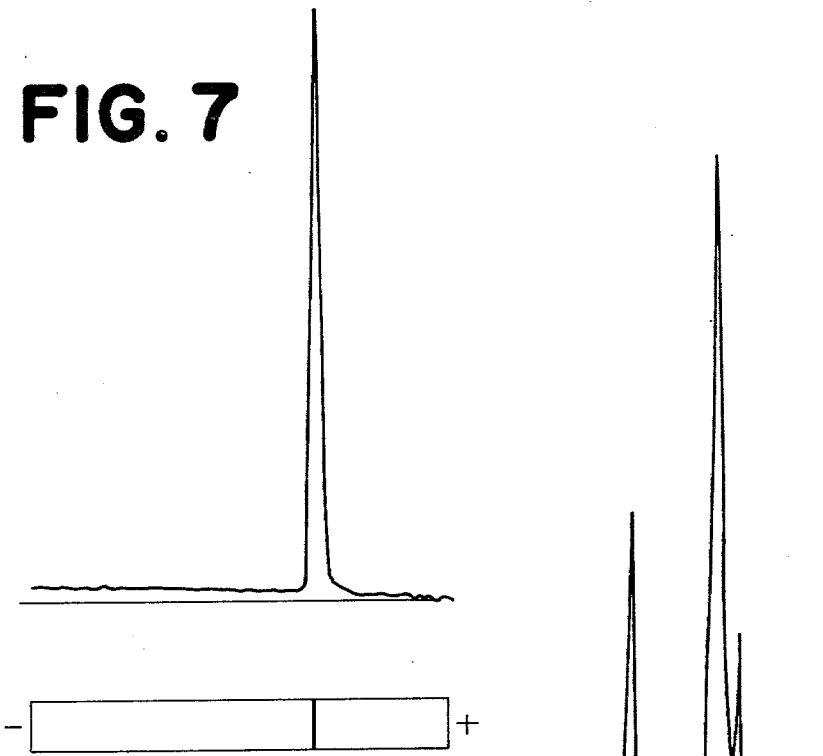
FIG. 7
FIG. 8
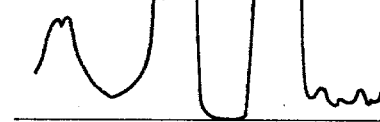

PROTEINIC ACTIVE SUBSTANCES

This invention relates to the novel elemental substances constituting an insulin secretory factor and various associated substances prepared from combinations of such elemental substances.

The present inventors have detected in the cells of the microorganisms belonging to Bordetella and in the supernatant of their culture medium a substance which has the amazing pharmacological activities to promote insulin secretion and to sustain the normal blood sugar level and which, therefore, is credited with high medicinal utility for treatment of diversified kinds of diabetes and as preventive thereof. The present inventors have also succeeded in isolation and chemical identification of this novel proteinic substance as an insulin secretion promoting factor. This substance demonstrates a prominent insulin secretion promoting activity at an extremely small dose (approximately 0.1 µg/kg body weight) and proves useful for treatment and prevention of various kinds of diabetes. It has been found, however, that this insulin secretion promoting factor produces, beside its said proper activities, the so-called side effects such as increasing leukocyte count and histamine sensitivity and encouraging antigenicity. For practical use of the substance as a medicament that is destined to be safe, it is essential to get rid of any unfavorable side effect without sacrificing the insulin secretion promoting activity proper to the substance. The present inventors have made efforts for attaining this object and succeeded in separating and purifying the insulin secretion promoting active factor into the elemental compositional substances, and further associations of these elemental substances have resulted in successful preparation of various novel associated compounds which are drastically lessened in side effects without compromising the insulin secretion promoting activity proper to said substances.

Now the attainments according to this invention are described in detail.

INSULIN SECRETION PROMOTING ACTIVE FACTOR

The insulin secretion promoting active factor (hereinafter referred to simply as "active factor"), which is the starting material in this invention, is a proteinic substance which can be obtained by culturing the microorganisms belonging to Bordetella known as pathogenic bacteria (such as pertussis bacillus, parapertussis bacillus and bronchial septicemia bacillus), most preferably *Bordetella pertussis phase I*, in a solid or liquid medium and collecting and purifying the proper substance from the cultured bacterial cells and culture medium.

Collection and purification of the active factor from the culture can be accomplished by any of a variety of methods generally employed in the art, such as precipitation method, chromatographic method, molecular sieve method, electrophoretic method and biological method, with these methods being used either singly or in suitable combinations, and hence this invention is not defined by any specific collecting and purifying method.

A column chromatographic process is suggested as an example of the highly advantageous active factor collecting and purifying methods. According to this process, the supernatant of the culture medium is passed through a column made of a filler such as Hydroxyapatite (Biochemical Industry Ltd.), CM-Sepharose Cl-6 B (Pharmacia Fine Chemicals), Con A-Sepharose-4 B (Pharmacia Fine Chemicals) or PAMA—Sepharose 6 MB mentioned later. The active factor is adsorbed to the column highly selectively and then eluted from a suitable selected elutant such as 0.1 M phosphate buffer (pH 7.0) containing 0.5 M NaCl. The purified product is then dialyzed to get rid of unnecessary salts, thus providing the pure active factor. The active factor is also present in the cultured bacterial cells, so that, if desired, said factor may be collected therefrom by, for example, adding NaCl to suspension to leach out the active factor into the solution.

The so-called ammonium sulfate precipitation method popularly used in the art is also available for preparation of the active factor. In this case, solid $(NH_4)_2SO_4$ is added to the supernatant of the culture to a point approximate to saturated solubility and pH is adjusted to 6 to 7 with dilute ammonia water. Then the precipitate is washed with water and the active factor is extracted from 0.1 M Tris buffer (pH 8) containing 0.5 M NaCl.

As aforesaid, pertussis bacillus, parapertussis bacillus and bronchiseptica bacillus are known as the Bordetella organisms that yield the active factor, but the variations of these pathogenic bacteria, such as those obtained from mutation by various known means such as change of medium composition, exposure to various kinds of radiation like ultraviolet rays or X-rays or use of a chemical mutagen, are also useful as another active factor source.

Any suitable method can be used for culture in this invention, though liquid shaking culture is preferred in respects of activity and yield.

As for the mycological properties and culture conditions of the microorganisms belonging to Bordetella, see Bergy's Manual of Determinative Bacteriology, Vol.8, 1974, Baltimore, The Williams & Willkins Co.; J. Exp. Med. 129, 523–550 (1969); and Mycological Training Handbook, 3rd Ed. p.6 ff., 1972, Maruzen & Co.

The chemical and physical properties of the active factor are as described below.

State of existence and solubility characteristics

The powder of the active factor obtained from freeze-drying after desalting is non-deliquescent, white or light brown, and dissolved in water at room temperature in concentration of up to about 3 to 5 mg/ml. When put into 6 N HCl, it forms an insoluble white precipitate. It is soluble in pyridine, dodecyl sodium sulfate, mercaptoethanol and cystine solution. Addition of a dry ice acetone or ethanol, trichloroacetic acid or zinc chloride solution or a solution containing several other types of metal ions to the solution of the purified active material at cold (4° C.) produces a white-turbid precipitate. When put into a mixed solution of water and chloroform or n-butanol, the active factor proves to be insoluble in such solution and gathers around the interface of both liquids.

When an aqueous solution of the active factor is heated to 80° C. or higher, it becomes white-turbid. Also, when this active factor is dissolved in 0.1 M phosphate buffer (pH 7.0) containing 0.5 M NaCl and then dialyzed by using distilled water as external liquid, said factor becomes white-turbid temporarily, but if dialysis is continued, the active factor is again perfectly dissolved and white turbidity disappears. If a high-concentration solution is subjected to thorough dialysis by using 0.01 M acetate buffer (pH 4.5), the active factor could be tinted in light brown and dissolved.

Molecular weight

The molecular weight of the active factor as determined by gel filtration through a column (2.8×80 cm) of Biogel P-100 (Bio. Rad Corp.) equilibrated with 0.1 M phosphate buffer containing 0.5 M NaCl was 77,000±6,400.

Composition

The protein content as determined according to the Lowry's method was over 95 wt% and the glucide content as measured by the phenol-sulfate method was apparoximately 1 wt%. The lipid concentration was below the lower limit of detection.

The following literatures were referred to for measurement of the respective components:

Protein

Lowry, O. H., N. J. Rosebrough, A. L. Farr and R. J. Randall: J. Biol. Chem. 193: 265, 1951.

Glucide

Phenol-$H_2SO_4$ method. Dobois, M., K. A., Giles, J. K. Hamilton, P. A. Rebers and F. Smith: Anal. Chem. 28 350, 1956.

Lipid

Total lipid and lipid conjugate were measured according to Marsh and Weinstein method (J. B. Marsh and D. B. Weinstein: J. Lipid Res., 7 574, 1966) by extracting the material before and after hydrolysis into chloroform, chloroform-methanol and heptane.

The amino acid composition of the protein component (compositional ratio μM/100 M, 16- or 24-hour hydrolysis at 110° C. in 6 N HCl):

Aspartic acid, 7.5–7.9; threonine, 6.8–7.6;
serine, 5.9–7.6; glutamic acid, 9.7–10.8;
proline, 5.5–6.4; glycine, 8.7–9.6;
alanine, 9.1–10.8; cystine/2, 1.5–2.6;
valine, 5.6–6.6; methionine, 2.5–3.3;
isoleucine, 3.6–4.1; leucine, 7.5–8.0;
tyrosine, 5.1–6.6; phenylalanine, 3.3–3.9;
lysine, 3.1–4.4; histidine, 1.4–1.6;
arginine, 6.1–6.6

Isoelectric point pH: 8.0±0.5

Disc electrophoretic pattern

The acrylamide (polyacrylamide concentration 7.5%, 1 N KOH-glacial acetic acid buffer (pH 4.3)) disc electrophoresis under the conditions of 30 μg specimen, current application of 4 mA, duration of 2 hr/gel, staining by amide black 10 B and destaining by 7% acetic acid solution gives a very sharp single band at the distance of 2.3±0.2 cm (with the spacer gel end as reference).

Biological properties

The active factor has an insulin secretion promoting action as well as a glucose tolerance improving acid for mammals, and these actions sustain for the period of several weeks to several months with a single dose. Acute toxicity ($LD_{50}$) is approximately 200 μg/kg body weight in ddy strain mice (intravenous injection).

ACTIVE FACTOR CONSTITUENTS (ELEMENTAL SUBSTANCES) AND ASSOCIATED SUBSTANCES THEREOF

1. Said active factor is separated into three different constituents (elemental substances) by column chromatography in the co-presence of a commonly known protein denaturant such as 8 M urea or 6 M guanidine hydrochloride, and these elemental substances were ascertained to be a single substance disc-electrophoretically.

Gel filtration in the presence of 8 M urea is recommended as an advantageous method for isolation and purification of the respective elemental substances. This method comprises dissolving the active factor in 0.1 M phosphate buffer (pH 7.0) containing 8 M urea and 0.5 M NaCl and then subjecting the mixture to gel filtration through a column of Sephacryl S-200 (Pharmacia Fine Chemicals) equilibrated with said buffer. As a result, the active factor is separated into three constituents with different molecular weights (they were named Proteinic Active Substances KS-I, KS-II and KS-III in the order of molecular weight), and additional gel filtration by the same column gives these constituents as a disc-electrophoretically single substance.

Another advantageous isolating and purifying method is DEAE cellulose (Celluba Co.,) column chromatography. In this method, the active factor is dissolved in 0.01 M phosphate buffer (pH 8.0) containing 8 M urea and then passed through a DEAE cellulose column equilibrated with the same buffer. Consequently, KS-I and KS-II are adsorbed to this column while KS-III is not adsorbed but flows down. KS-I is eluted by 0.02 M phosphate buffer (pH 7.0) containing 8 M urea while KS-II is eluted by 0.05 M phosphate buffer (pH 6.0).

These elemental substances are provided as a disc-electrophoretically single substance on gel filtration through a column of Sephacryl S-200 equilibrated with 0.1 M phosphate buffer containing 4 M urea and 0.5 M sodium chloride.

The thus obtained elemental substances KS-I, KS-II and KS-III exhibit per se a lower insulin secretion promoting activity than the original active factor, but the "side effects" such as leukocytosis promoting action, histamine sensitivity increasing action and antigenicity are nonuniformly distributed in the respective materials and thereby attenuated.

It was also ascertained that KS-I and KS-II are acidic proteins while KS-III is a basic protein.

Under some conditions of resolution of the active factor into the composing substances thereof, any one of the elemental substances can be further resolved into more small peptide fragments. For example, the resolution of the active factor by using 0.1 M phosphate buffer solution containing 4 M urea, 1% 2-mercaptoethanol and 0.5 M NaCl followed by gel filtration through Sephacryl S-200 column equilibrated with said buffer provides five peptide fragments which include further two additional fragments to the three elemental substances.

Accordingly, the process of this invention relates to the general resolution treatment of the active factor into the composing peptide fragments thereof which may include at least one of the elemental substances.

2. It was also disclosed that the substances KS-I, KS-II and KS-III, although dormant per se in insulin secretory activity, become strongly active in promoting insulin secretion and in suppressing said various side effects and toxicity when they are combined together in certain groups. That is, combinations of KS-I and KS-III, KS-II and KS-III, and KS-I, KS-II and KS-III produce strong activity, but the combination of KS-I and KS-II is almost inactive. The fact was also unveiled by further studies that these materials are associated with each other in a certain buffer solution to form a single proteinic associated compound. Thus, when the combinations of the substances KS-I and KS-III, KS-II and KS-III, KS-I, KS-II and KS-III, and KS-I and KS-II are reacted and associated with each other in a certain buffer solution, there are produced the disc-electrophoretically single proteinic associated compounds which were named associated substances KSA-I, KSA-II, KSA-III and KSA-IV, respectively.

An example of the advantageous method for producing these proteinic associated substances is shown below.

The respective combinations of the elemental substances are mixed, at the rates of KS-I:KS-II=5:1 in the case of KSA-I, KS-II:KS-III=2:1 in the case of KSA-II, KS-I:KS-II:KS-III=5:2:2 in the case of KSA-III, and KS-I:KS-II=2:1 in the case of KSA-IV (all by protein weight), in a 0.1 M phosphate buffer (pH 7.0) containing 2 M urea and 0.5 M sodium chloride and then subjected to 24-hour shaking at 37° C., whereby the substances in the respective combinations are associated with each other. Then these mixed solutions are concentrated and subjected to gel filtration through a column of Sephacryl S-200 equilibrated with 0.1 M phosphate buffer (pH 7.0) containing 2 M urea and 0.5 M sodium chloride or to ion exchange chromatography to separate the associated substances and the non-associated elemental substances, thereby obtaining the single associated substances KSA-I, KSA-II, KSA-III and KSA-IV respectively. The yield of these associated products varies greatly depending on the treating conditions such as temperature, pH, time, density and ion strength.

It was also found that these novel proteinic associated substances, although substantially equal to the active factor in their primary activity, are less than 1/50 in the leukocytosistic activity, less than 1/10 in the histamine sensitivity increasing activity, less than 1/25 in antigenicity and less than 1/3 in LD$_{50}$ value as compared with the active factor.

3. Properties and solubility of the elemental and associated substances:

The refined powders of all the desalted and freeze-dried elemental and associated substances are non-deliquescent white powders. KS-III, KSA-II and KSA-III are soluble in water to the degree of 1 mg/ml at room temperature while the others are sparingly soluble in water but soluble to the extent of the 4 mg/ml in 0.1 M phosphate buffer containing 4 M urea and 0.5 M NaCl.

The aqueous solutions of the respective substances become white turbid and form precipitates when added with ammonium sulfate, dry ice acetone, ethanol, trichloacetic acid or such at cold (4° C.). Also, each of the substances, when put into a mixed solution of water and chloroform or n-butanol, gathers around the interface of both liquids.

Molecular weight:

The molecular weights of the respective elemental substances as determined by gel filtration through a column (1.5×95 cm) (Pharmacia Fine Chemicals) of Sephacryl S-200 equilibrated with 0.1 M phosphate buffer (pH 7.0) containing 8 M urea and 0.5 M NaCl are as follows: KS-I, 63,000±5,200; KS-II, 31,000±4,500; KS-III, 12,500±1,500. The molecular weights of the respective associated substances as determined by using a column (1.5×95 cm) of Sephacryl S-200 equilibrated with 0.1 M phosphate buffer (pH 7.0) containing 4 M urea and 0.5 M NaCl are as follows: KSA-I, 75,000±8,500; KSA-II, 35,000±4,500; KSA-III, 85,000±13,000, KSA-IV, 88,000±6,300.

Isoelectric point pH;

The isoelectric point pH's of the respective substances as measured by using acrylamide gel electrofocussing technique are as follows: KS-I, 5.6±0.3; KS-II, 5.4±0.4; KS-III, 8.3±0.3; KSA-I, 6.8±0.4; KSA-II, 6.3±0.3; KSA-III, 8.2±0.5; KSA-IV, 5.6±0.4.

Compositions:

|  | Protein (Lowry's method) | Glucide (phenol-sulfuric acid method) |
| --- | --- | --- |
| KS-I | > 97 | 1.3 ± 0.4 |
| KS-II | > 95 | 1.2 ± 0.3 |
| KS-III | > 96 | 1.5 ± 0.6 |
| KSA-I | > 96 | 1.3 ± 0.3 |
| KSA-II | > 96 | 1.3 ± 0.4 |
| KSA-III | > 96 | 1.3 ± 0.2 |
| KSA-IV | > 95 | 1.3 ± 0.3 |

(Note) All figures are used by weight %.

Amino acid composition of protein component and percentage composition ($\mu$M/100 $\mu$M):

|  | KS-I | KS-II | KS-III |
| --- | --- | --- | --- |
| Aspartic acid (Asp) | 8.1 | 9.3 | 5.3 |
| Threonine (Thr) | 8.5 | 7.7 | 4.8 |
| Serine (Ser) | 7.9 | 9.8 | 6.2 |
| Glutamic acid (Glu) | 9.6 | 11.8 | 9.6 |
| Proline (Pro) | 5.0 | 4.6 | 9.3 |
| Glycine (Gly) | 10.0 | 9.8 | 8.1 |
| Alanine (Ala) | 9.5 | 11.3 | 9.3 |
| ½ cystine (½ Cys) | 1.1 | N.D. | 2.3 |
| Valine (Val) | 6.2 | 7.4 | 10.2 |
| Methionine (Met) | 1.8 | 1.9 | 6.0 |
| Isoleucine (Ile) | 4.5 | 4.0 | 2.2 |
| Leucine (Leu) | 6.5 | 5.3 | 8.6 |
| Tyrosine (Tyr) | 7.6 | 6.2 | 2.5 |
| Phenylalanine (Phe) | 2.8 | 2.5 | 4.5 |
| Lysine (Lys) | 2.1 | 1.9 | 5.8 |
| Histidine (His) | 1.6 | 1.1 | 0.5 |
| Arginine (Arg) | 7.3 | 5.4 | 4.8 |

(Note) Hydrolyzed in 6N hydrochloric acid at 110° C. for 16 hours.

EXAMPLE I

Preparation and purification of active factor

1. Freeze-dried and preserved *Bordetella pertussis* (phase I, Maeno Strain) bacterium was plate-cultured in Bordet-Gengou medium at 37° C. for 2 days, and then a platinum loopful of said bacterium was inoculated into a 500 ml shaking flask in which 200 ml of an ion exchange resin added modified Cohen-Wheeler medium (CW medium) having the composition shown in Table 1 below had been pipetted, and then subjected to 20- to 22-hour shaking culture at 37° C. The bacterium concentration in the culture solution was measured by a spectrophotometer (wavelength: 650 nm), and this solution was added into a 2-liter shaking flask, which has pipetted therein 1 liter of the ion exchange resin added CW medium, such that the final bacterium concentration would become approximately $0.1 \times 10^9$ cells/ml, and this was followed by 48-hour shaking culture (shaking frequency: 97 times/min) at 37° C.

The mycological properties of the above-said strain agreed with those described in the afore-cited literature concerning the pertussis phase I strains.

Table 1

| Composition of modified Cohen-Wheeler medium | |
|---|---|
| Casamino acid | 1.0 g |
| Yeast extract | 1 g |
| Potassium dihydrogenphosphate | 0.5 g |
| Soluble starch | 2 g |
| 0.5% copper sulfate solution | 1 ml |
| 1% calcium chloride solution | 1 ml |
| 4% magnesium chloride solution | 1 ml |
| Polypeptone | 5 g |
| 1% cystine solution | 2.5 ml |
| 0.5% iron sulfate solution | 1 ml |
| Sodium chloride | 2.5 g |

(In use of this liquid medium, it was added with distilled water to make the total amount 1,000 ml and, after adjusting pH to 7.2 with 20% NaOH solution, the medium solution was further added with 3 gr of an anion exchange resin (Diaion SA-20 AP, Mitsubishi Kasei Co.) and then subjected to 15-minute high pressure steam sterilization at 121° C.)

The obtained 48-hour shaking culture solution was heated at 56° C. for 30 minutes and then centrifuged (at 15,000 r.p.m.) at 4° C. to separate into the supernatant and the bacterium cells, and the thus obtained supernatant of the culture solution was used as starting material for refining and isolation of the object active factor.

10 liters of this supernatant, after adjusted to pH 6.0 with 1 N HCl, was passed through a hydroxyapatite column (2.5×4 cm) at the flow rate of 200 ml/hr as the first purifying step.

Most of protein passed by the column without adsorbed thereto, and the object insulin secretory activity (see the activity measuring method described later) was scarcely detected. The protein concentration was measured by the Lowry et al method noted at the bottom of Table 2 shown later.

To determine the adsorbed substances, the column was first washed with 0.01 M phosphate buffer (pH 6.0) and then, after elevating the molar concentration of the phosphate buffer to 0.1 and pH to 7.0, the adsorbed proteins were eluted out successively. However, the object active factor was not eluted under this condition. So, additional elution was performed with a phosphate buffer of the same composition but containing 0.5 M NaCl. Under this condition, the object active factor could be recovered at high efficiency in agreement with the eluted portein (FIG. 1).

Figure 2:
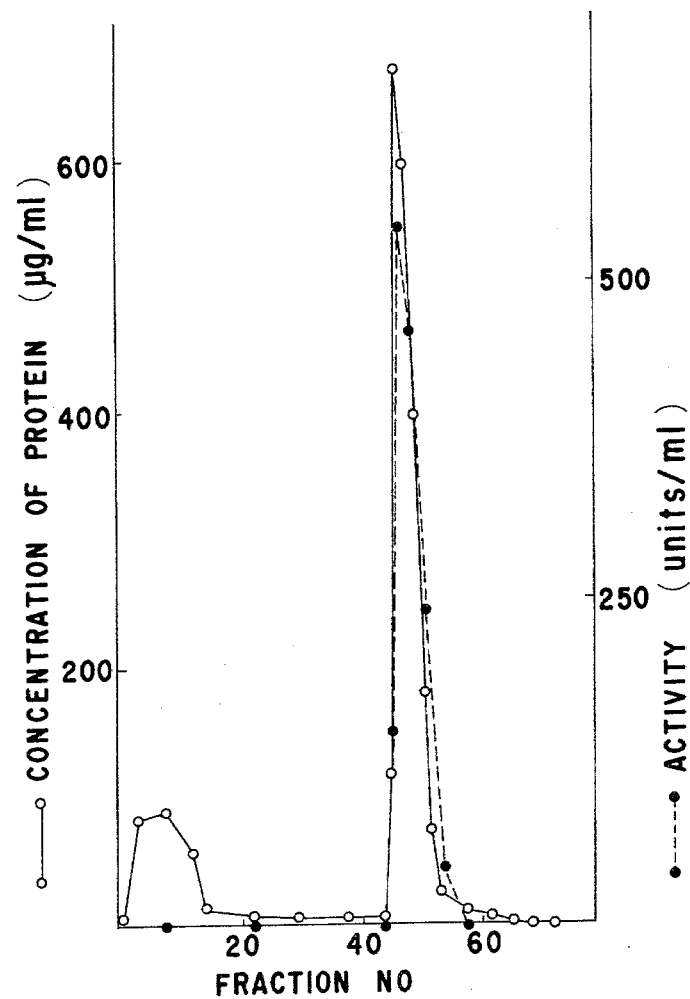

The obtained active factor was concentrated, and after placing it in a dialysis membrane (Thomas Cat. No. 3787-F25) with maximum permeable molecular weight 8000, it was dialyzed twice (for total 12 hours) with distilled water and twice (for total 12 hours) with 0.01 M phosphate buffer (pH 6.0). For further refining, the solution containing the dialyzed active factor was passed through a column (1.5×10 cm) of Carboxymethyl Sepharose CL-6B equilibrated with 0.01 M phosphate buffer (pH 6.0). The materials not adsorbed to this column had no activity. Then, after elevating molar concentration and pH of the phosphate buffer to 0.1 and 7.0, respectively, the similar elution was performed by adding 0.5 M saline, whereby there was obtained the object active factor agreeing with the eluted protein (FIG. 2).

Since this product still contained a slight quantity of impurities in the disc electrophoretic sense, this active factor was further concentrated and, after placed in a dialysis membrane (of the same standard as said above), dialyzed twice (for total 12 hours) with distilled water and twice (for total 12 hours) with 0.01 M phosphate buffer (pH 7.0), and the dialyzed specimen was passed through a column (1.5×8 cm) of Con A-Sepharose 4 B which had been equilibrated with 0.01 M phosphate buffer (pH 7.0).

Figure 3:
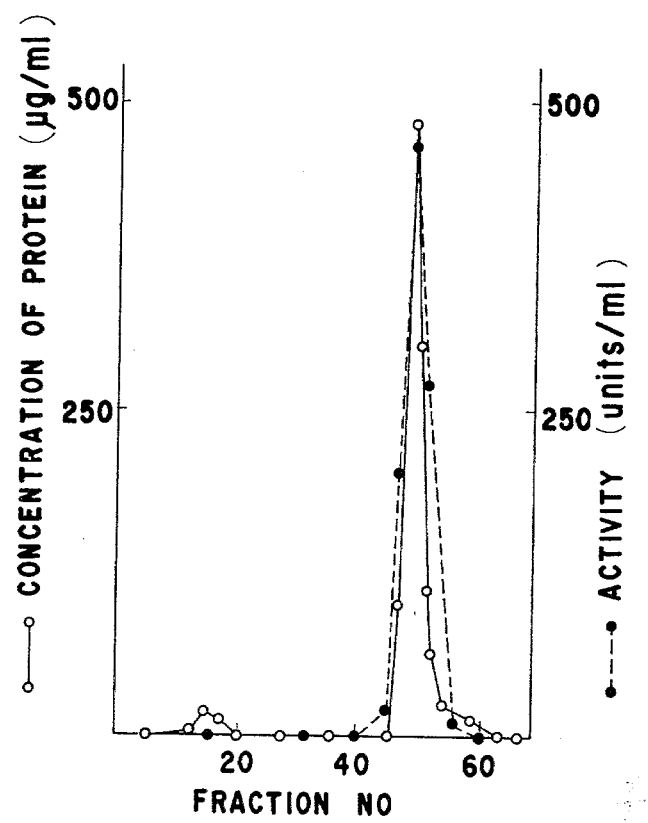

Development with the ame buffer eluted a trace amount of protein, but this protein portion had no activity. Further elution with 0.1 M phosphate buffer (pH 7.0) containing 0.5 M NaCl gave the active factor agreeing with the eluted protein (FIG. 3).

Figure 4:
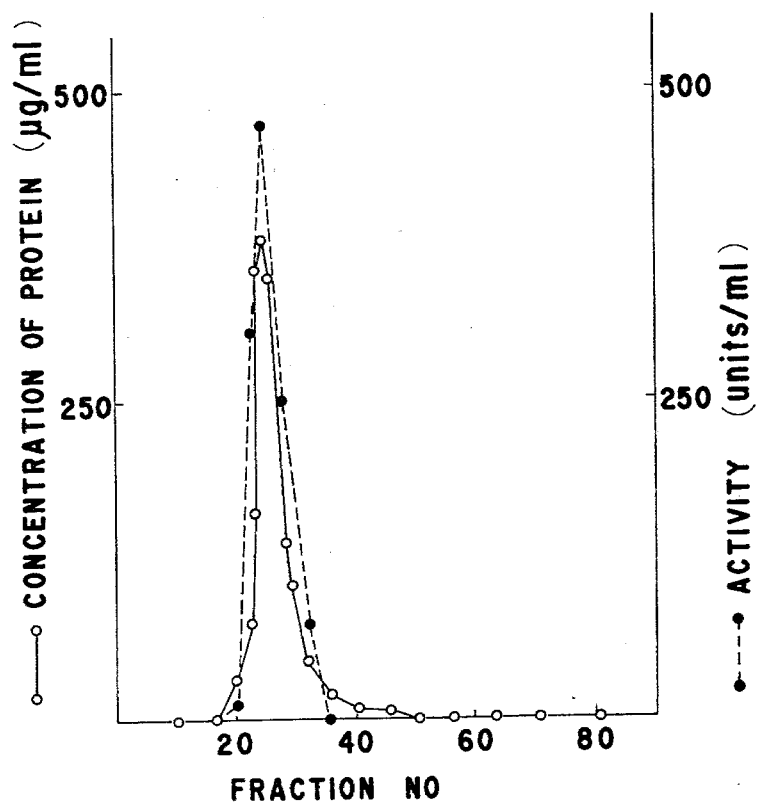

Since this protein portion stilled contained a minute quantity of impurities in the disc electrophoretic sense, this protein portion was amassed and concentrated and dialyzed with 0.01 M phosphate buffer (pH 7.0) containing 0.5 M NaCl, and the dialyzed specimen was subjected to gel filtration through a column (2.8×60 cm) of Biogel P-100 (Rio. Rad Co.) equilibrated with the same buffer. This produced the pure active factor agreeing with the protein portion showing the peak at the molecular weight level of around 80,000 (FIG. 4).

Activity recovery, purification and other data obtained in this purification step are shown in Table 2. Property assay of this substance is as described in the preceding clause "Insuline secretion promoting active factor".

Table 2

| Steps | Solution quantity (ml) | Protein concentration (μg/ml) | Specific activity (units/μg) | Activity yield (%) | Purification |
|---|---|---|---|---|---|
| Supernatant of culture medium | 10,000 | 2,300 | 0.84 | 100 | 1 |
| Hydroxyapatite col. chrom. | 130 | 160 | 759 | 82 | 904 |
| CM-Sepharose col. chrom. | 52 | 210 | 1005 | 57 | 1196 |
| Con A-Sepharose col. chrom. | 50 | 164 | 1217 | 52 | 1449 |
| Biogel P-100 col. chrom. | 43 | 158 | 1342 | 47 | 1598 |

(Note) The protein concentration was measured by Lowry et al method (Lowrey, O,H, N.J. Rosenbrough, A.L. Farr and R.J. Randall: J. Biol. Chem. 193, 265, 1951) and the bovine serum albumin was used for standard.

The purity of the substance obtained in the above-described final step was determined according to disc electrophoresis with polyacrylamide gel (polyacrylamide concentration, 7.5%, 1 N KOH-glacial acetate buffer (pH 4.3)).

The method of J. V. Maizel, Jr. (Biochem. Biophys. Res. Comm., 1963, 13, 483) was employed for the experimental process.

Figure 5:
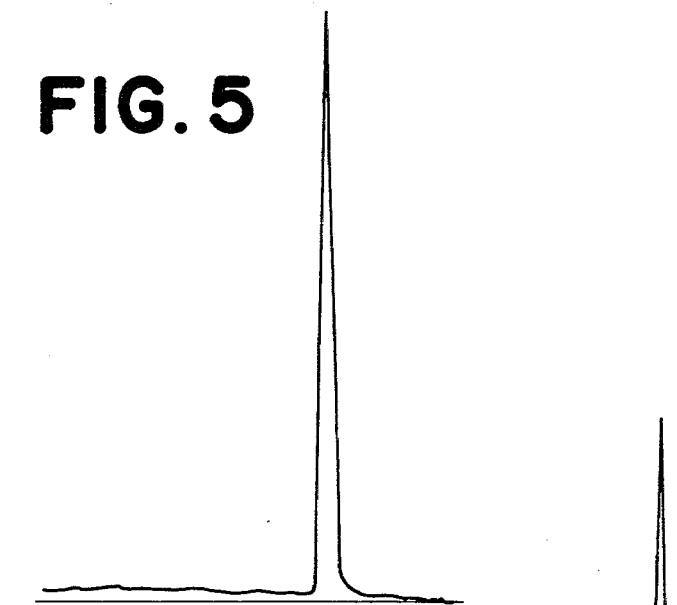

The amount of the specimen per gel was 30 μg (as protein), and the experiment was conducted by applying current of 4 mA for 2 hours, staining with amide black 10B and destaining with 7% acetic acid solution. The obtained results are shown in FIG. 5 (a drawing of gel condition and an electrophoretic diagram obtained by using a dencitometer). It was ascertained that the specimen obtained in this final step is a single substance perfectly free of impurities, and that the insulin secretion promoting activity defined in Example 1 well agreed with this isolted substance. For determining the subunit structure of this substance, it was subjected to the following SDS (sodium dodecylsulfate) disc electrophoresis according to the Shapilo et al method (A. L. Shapilo et al; Biochem. Biophys. Res. Comm., 1967, 28, 815).

Figure 6:
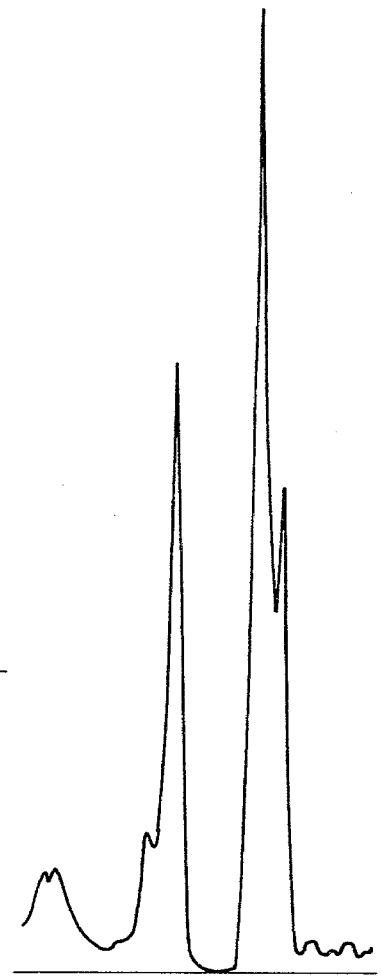

50 μg/tube (as protein) of this substance was added to a mixture of 1% SDS, 1% mercaptoethanol and 4 M urea, and after 2-hour incubation at 37° C., the mixture was applied to 10% polyacrylamide gel containing 1% SDS, and after 4-hour current application of 8 mA/gel, stained with Coomsie Blue and destained with 7.5% acetic acid. The results are shown in FIG. 6 (a gel condition drawing and an electrophoretic diagram by use of a dencitometer).

2. Freeze-dried and preserved *Bordetella pertussis* phase I Tohama Strain bacterium (supplied by Department of Bacteriology, Kitasato University School of Pharmaceutical Sciences) was cultured in a Bordet-Gengou medium (BG medium) containing 20% of defibrinated horse blood at 37° C. for 3 days, followed by 20- to 24-hour culture in BG slant medium at 37° C., and then a platinum loopful of the cultured bacterium was inoculated into a 500-ml shaking flask which had previously pipetted thereinto 200 ml of an ion exchange resin added semi-synthetic liquid medium (modified Cohen-Wheeler liquid medium—CW medium) having the composition shown in Table 3 below, followed by 20- to 24-hour shaking culture at 37° C.

The bacterium concentration in the culture solution was measured by a spectrophotometer (wavelength: 650 nm), and the solution was added into a 2-liter shaking flask, which had already pipetted thereinto 1 liter of said CW medium, such that the final bacterium concentration would become 0.07 to $0.15 \times 10^9$ cells/ml, and subjected to 4-hour shaking culture at 37° C. (shaking frequency: 100 to 120 times/min).

The obtained 48-hour shaking culture solution was heated at 56° C. for 30 minutes and then centrifuged (at 15,000 r.p.m.) at 4° C. to separate into the supernatant and the bacterium cells.

Table 3

| Modified Cohen-Wheeler medium composition (semi-synthetic liquid medium) | | |
|---|---|---|
| Casamino acid | 10 | g |
| Yeast extract | 1 | g |
| Potassium dihydrogenphosphate | 0.5 | g |
| Soluble starch | 2 | g |
| 0.5% copper sulfate solution | 1 | ml |
| 1% calcium chloride solution | 1 | ml |
| 4% magnesium chloride solution | 1 | ml |
| Polypeptone | 5 | g |
| 1% cystine solution | 2.5 | ml |
| 0.5% iron sulfate solution | 1 | ml |
| Sodium chloride | 2.5 | g |

In use of this liquid medium, it was added with distilled water to make the total quantity 1,000 ml, and after adjusted to pH 7.2 with 20% NaOH solution, it was further added with 3 gr of an anion exchange resin (Diaion SA-20AP by Mitsubishi Kasei Co.) and then subjected to 15- to 20-minute high pressure steam sterilization at 121° C.

10 liters of the thus obtained supernatant of the culture medium was passed through a hydroxyapatite column (5×2 cm, flow rate: 60 ml/hr) and then washed with 100 ml of 0.01 M phosphate buffer (pH 6.0). This was followed by flowing of 300 ml of 0.1 M phosphate buffer (pH 7.0), and finally, 0.1 M phosphate buffer (pH 7.0, containing 0.5 M sodium chloride) was flown at the flow rate of 15 ml/hr to elute out the object active factor. The obtained active factor was concentrated to approximately 15 ml with polyethylene glycol (average molecular weight 20,000) and then dialyzed four times for the total period of 24 hours with 2 liters of distilled water and further dialyzed four times for the total period of 24 hours with 1 liter of 0.01 M phosphate buffer (pH 6.0) to equilibrate. The product was then passed through a column (1.5×10 cm) of Carboxymethyl Sepharose CL-6B (Pharmacia Fine Chemicals) equilibrated with the same buffer as said above. No activity was detected in the materials which were not adsorbed to the column. After elevating the molar concentration and pH of the phosphate buffer to 0.1 M and 7.0, respectively, similar treatment was performed by adding 0.5 M sodium chloride, producing the active factor agreeing with the eluted protein. This active factor was concentrated to approximately 10 ml and then dialyzed four times for the total period of 24 hours with 2 liters of distilled water, followed by four-times 24-hour dialysis and equilibration with 1 liter of 0.01 M phosphate buffer (pH 4.5, containing 0.1 M sodium chloride, or pH 4.5, containing 0.1 M lithium chloride-hydrochloric acid). This solution was passed, at the flow rate of 5 ml/hr, through a column (1.2×8 cm) of P-acetoxymercurianiline Sepharose 6MB (see the preparation method described below) equilibrated with the same buffer, followed by sufficient washing with the same buffer (about 200 ml), and the adsorbed material was eluted with the same buffer added with 0.01 M L-cystine. Absolutely no active factor was contained in the nonadsorbed portion, and the active factor was obtained concentratedly in the final elutant. This active factor was dialyzed six times for the total period of 48 hours with 2 liters of distilled water and then freeze-dried to obtain 7.3 mg of light brown powder. This product gave a single band on polyacrilamide gel electrophoresis (using gel of pH 4.3) as shown in FIG. 7 and its isoelectric point pH was 7.8±0.5. Also, it had the composition of about 92 wt% protein, 1.8 to 5.6 wt% glucide and 0 to 2 wt% lipid, and its amino acid composition was shown in Table 4. The molecular weight of this substance as measured by gel filtration (using Biogel P-150, column size: 1.8×95 cm, buffer: 0.01 M acetate buffer with pH 4.5) was assumed to be 51,000±4,300. The activity recovery, purification and other data obtained in the foregoing final step were as shown in Table 5. The SDS disc electrophoresis (1% SDS, 1% mercaptoethanol and 4 M urea) gave three bands as shown in FIG. 8. The insulin secretion promoting activity was 1,349 U/μg and acute toxicity $LD_{50}$ was 232 μg/kg in male mice and 174 μg/kg in female mice.

(Note) Method of preparation of P-acetoxymercurianiline (PAMA)—Sepharose 6MB:

4 gr of CNBr-activated Sepharose 6MB (Pharmacia Fine Chemicals) is repeatedly washed and swollen on a glass filter byusing 1 liter of $10^{-3}$N HCl. There is separately prepared a solution by dissolving 172 mg (0.5 mM) of P-acetoxymercurianiline in 50 ml of 60% dimethylformamide solution of 0.1 M sodium hydrogencarbonate buffer (pH 8.3, containing 0.5 M sodium chloride). Upon completion of washing and swelling of the gel, the above-said solution is added and the mixture is well shaken at room temperature (22° to 25° C.) for 2 hours. After completion of the reaction, the product is washed well with the same buffer, and after adding 50 ml of 1 M ethanolamine (pH 9.0) to the gel, the mixture is well shaken at room temperature for 2 hours. Then the gel is suction filtered with a glass filter, washed several times alternately with 1 liter of 0.1 M borate buffer (pH 8.5) and 1 liter of 0.1 M acetate buffer (pH 4.0), and finally equilibrated with 0.01 M acetate buffer (pH 4.5, containing 0.1 M sodium chloride) or 0.1 M lithium chloride-hydrochlorite buffer (pH 4.5). Otherwise, the gel is previously treated with the same buffer containing 1% 2-mercaptoethanol and then sufficiently washed and equilibrated with the same buffer.

Table 4

Amino acid composition
(hydrolyzed in 6N HCl at 110° C. for 16 hours)

| Asp | 7.2  | Cys/2 | 1.7 | Lys | 3.5 |
|-----|------|-------|-----|-----|-----|
| Thr | 7.3  | Val   | 4.9 | His | 1.7 |
| Ser | 7.5  | Met   | 2.6 | Arg | 6.9 |
| Glu | 10.0 | Ile   | 3.8 |     |     |
| Pro | 6.5  | Leu   | 7.5 |     |     |
| Gly | 9.3  | Tyr   | 6.5 |     |     |
| Ala | 9.7  | Phe   | 3.4 |     |     |

$\mu M/100\mu M$

Table 5

| Steps | Solution quantity (ml) | Protein concentration ($\mu$g/ml) | Total protein (mg) | Specific activity (units/$\mu$g) | Yield (%) | Purification |
|---|---|---|---|---|---|---|
| Supernatant of culture medium | 10,000 | 3.500 | 35.000 | 0.56 | 100 | 1 |
| Hydroxyapatite col. chrom. | 90 | 270 | 24.3 | 647.3 | 80.3 | 1155.9 |
| CM-Sepharose col. chrom. | 53 | 235.9 | 12.5 | 862.0 | 55.0 | 1539.3 |
| PAMA Sepharose col. chrom. | 65 | 112.3 | 7.3 | 1349.0 | 50.2 | 2408.9 |

EXAMPLE II

Figure 9:
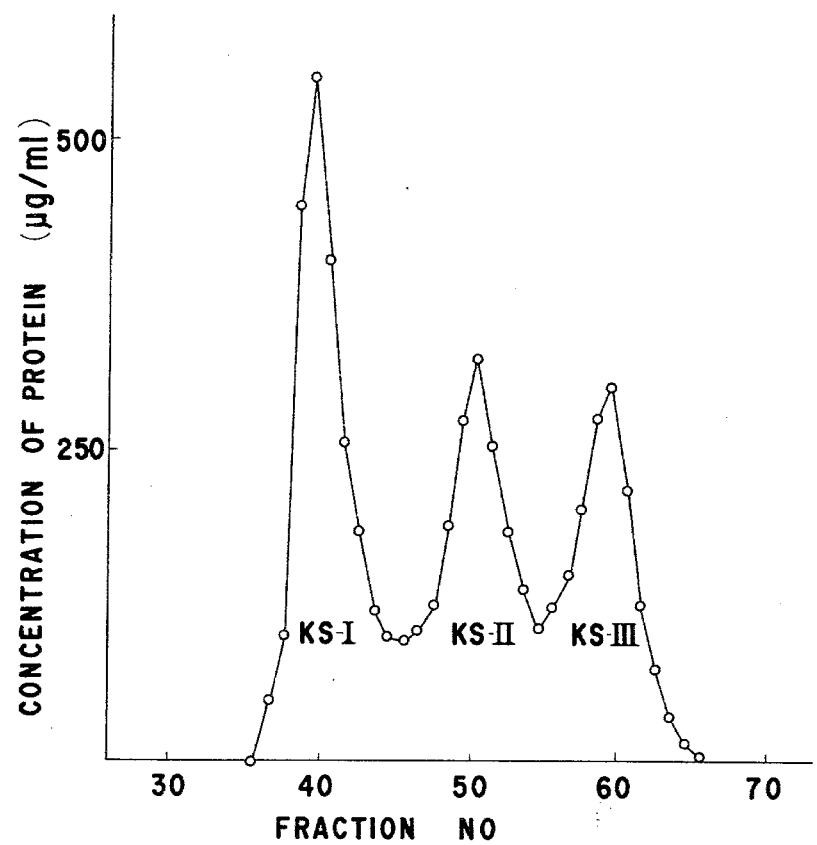

Preparation and purification of elemental substances 1. 20 mg of purified insuline secretion promoting active factor (purified preparation of Example I-1) was dissolved in 3 ml of 0.1 M phosphate buffer (pH 7.0) containing 8 M urea and 0.5 M sodium chloride, and after allowing the mixture to stand at 37° C. for 2 hours, the mixture was subjected to gel filtration through a column (1.5×95 cm) of Sephacryl S-200 equilibrated with the same buffer. The results are shown in FIG. 9. By this operation, the active factor was separated into the three components with different mocecular weights (they were named KS-I, KS-II and KS-III in the order of molecular weight as aforesaid). In order to further purify these component substances, their fractions were gathered, concentrated and then subjected to gel filtration by using the same column.

Figure 10:
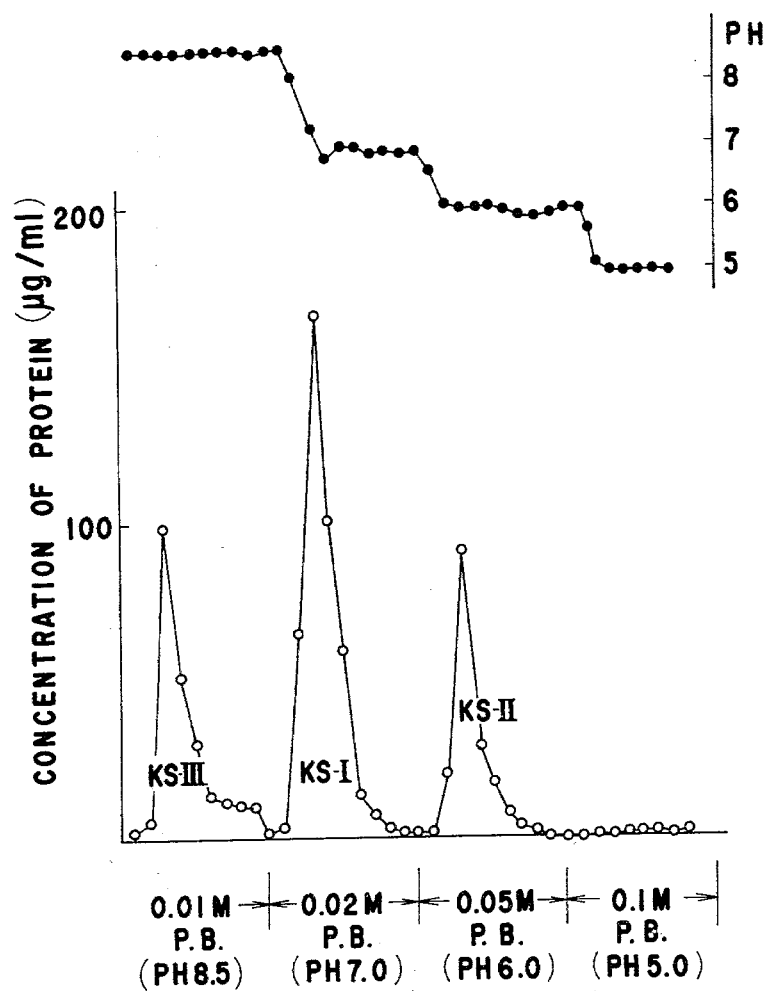

2. 20 mg of purified insulin secretion promoting active factor (purified preparation of Example I-2) was dissolved in 3 ml of 0.01 M phosphate buffer (pH 8.5) containing 8 M urea, and after allowing the mixture to stand at 37° C. for 2 hours, it was passed through a column (1.5×20 cm) of DEAE cellulose equilibrated with the same buffer. KS-III passed by the column without adsorbed thereto, but KS-I and KS-II were adsorbed to the column. KS-I was eluted with 0.02 M phosphate buffer (pH 7.0) containing 8 M urea and KS-II was eluted with 0.05 M phosphate buffer (pH 6.0). This elution pattern is shown in FIG. 10. In order to further purify these component materials, they were concentrated and then subjected to gel filtration through a column (1.5×95 cm) of Sephacryl S-200 equilibrated with 0.1 M phosphate buffer (pH 7.0) containing 8 M urea and 0.5 M sodium chloride.

Figure 11:
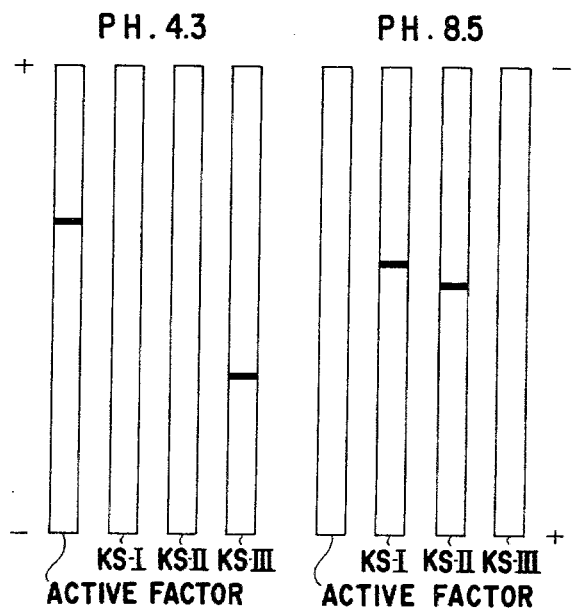
Figure 12:
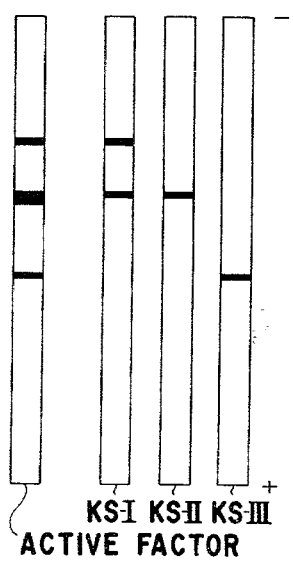

3. The elemental substances isolated and purified in the above-described examples were ascertained to be a disc-electrophoretically single substance as illustrated in FIG. 11. FIG. 12 shows the results of a comparative examination of the insulin secretion promoting active factor and the respective elemental materials according to SDS polyacrylamide gel electrophoresis. It will be noted that KS-I has two 1:1 subunits on the high molecular side of the active factor and KS-II corresponds to a subunit of intermediate molecular weight of the active factor, while KS-III agrees with a subunit of low molecular weight. The property values of the respective elemental materials are as described in "Properties of elemental materials and associated substances". The experimental conditions for electrophoresis were same as used in Example I-1.

EXAMPLE III

Production and purification of associated substances

The elemental substances KS-I, KS-II and KS-III obtained in Example II are associated in suitable combinations to produce the novel insulin secretion promoting associated substances named KSA-I (association of KS-I and KS-III), KSA-II (association of KS-II and KS-III), KSA-III (association of KS-I, KS-II and KS-III) and KSA-IV (association of KS-I and KS-II).

The optimum conditions for preparation of these associated substances KSA-I, KSA-II, KSA-III and KSA-IV are as follows. In the case of KSA-I, KS-I and KS-III are mixed in the ratio of 5:1 in an aqueous solution and, after adjusting pH to 7.0, the mixture is shaken at 37° C. for more than 24 hours. As for KSA-II, KS-II and KS-III are mixed in the ratio of 2:1 and, after pH adjustment to 7.0, the mixture is shaken at 37° C. for more than one hour. For KSA-III, KS-I, KS-II and KS-III are mixed in the ratio (by protein loading) of 5:2:2, followed by pH adjustment of 7.0 and 24-hour shaking at 37° C., and for KSA-IV, KS-I and KS-II are mixed in the ratio of 2:1, followed by pH adjustment to 7.0 and 24-hour shaking at 37° C.

All of these associated substances can be obtained in a yield of higher than 95% under the said conditions, but in order to eliminate the non-associated elemental materials, the products are further subjected to gel filtration through a column (1.5×95 cm) of Sephacryl S-200 equilibrated with 0.1 M phosphate buffer (pH 7.0) containing 2 M urea and 0.5 M sodium chloride. By this operation, all of the associated substances are obtained as a disc-electrophoretically single compound.

Even if this preparation process is carried out outside the range of the above-said optimum conditions, it is possible to obtain the object associated substances, but in a poor yield.

The property values of the respective associated substances isolated and purified in this example are same as described in the preceding article "Properties of elemental materials and associated substances".

EXAMPLE IV

Pharmacological effects

1. Determination of insulin secretion promoting activity

The insulin secretion promoting activity of each active substance can be determined by measuring animal reaction to various kinds of insulin secretion stimulants, and usually glucose is used as stimulant for this purpose.

Test animals
Wistar male rats (with body weight of 130 to 140 gr).
Testing method The active substances with diverse strengths are dissolved in a physiological saline solution, and 0.2 ml of each of these solutions is injected intravenously, under ether anesthesia, into the femoral vein of the test rats, and the insulin secretion promoting activity of each substance is measured three days later. The rats are fasted for 18 to 20 hours before the experiment. For measurement of activity, 0.1 ml of blood is collected from the tail vein of each rat, immediately followed by intraperitoneal injection of a 30% glucose solution in an amount of 1 ml per 100 gr body weight, and precisely 15 minutes later, 0.1 ml of blood is again collected in the similar way. The insulin secretion promoting activity is determined from the differences in blood sugar level and insulin concentration in blood before and after the glucose challenge. Blood sugar level is measured by the glucose oxidase method and insulin concentration by the double antibody method described below. Blood sugar level: Glucose oxidase method Bergmeyer, H. -U., and Bernet, E. in "Methods of enzymatic analysis", Bergmeyer, H. -U., eds, New York Academic Press P 123 (1963).
Insulin concentration: Double antibody method Morgan, C. R., and Razarow, A.: Diabetes, 12 115 (1963) Insulin immunoassay kit by Dainabot Inc.

Firstly, the $\Delta I/\Delta G$ values of the active substance administered group and the control group are obtained from the following equation:

$$\Delta I/\Delta G \, (\mu U/mg) = \frac{\text{Plasma insulin concentration after glucose load } (\mu U/ml) - \text{Plasma insulin concentration before glucose load } (\mu U/ml)}{\text{Blood glucose concentration after glucose load } (mg/ml) - \text{Blood glucose concentration before glucose load } (mg/ml)}$$

Use of blood sugar level for calculation of activity is for the reason that the amount of insulin secreted is greatly affected by the blood sugar level.

Strength of each active substance is given by the following equation:

$$\text{Unit} = \frac{\text{Average } \Delta I/\Delta G \text{ of treated group} - \text{Average } \Delta I/\Delta G \text{ of control group}}{\text{Average } \Delta I/\Delta G \text{ of control group}} \times 100$$

Specific activity of each substance is given by dividing unit strength by weight.

2. Determination of immuno potentiating activity

The immuno potentiating activity of the active substances can be measured in various experimental systems. Shown below is a method making use of adjuvant activity in a liquid antibody producing system.

Test animals
Female rats of Wistar strain (body weight 200±10 g)
Male rats of Wistar strain (body weight 250±20 g)
Testing method Dinitrophenyl-Ascaris (DNP-AS) prepared by bonding dinitrophenyl group to the protein obtained from Ascaris suum is used as antigen, and 1 ml of this antigen and various active substances are dissolved in 0.5 ml of a physiological saline, and the thus prepared solutions are subcutaneously injected to the soles of both front and rear limbs of male rats under ether anesthesia for primary immunization. As control, 1 mg of DNP-AS is dissolved in 0.5 ml of a physiological saline containing $10^{10}$ of dead B. pertussis bacterial cells and similarly sensitized to effect primary immunization. 5 days after primary immunization, 0.5 ml of the physiological saline containing 0.5 mg of DNP-AS is injected to the back muscle of the rats under ether anesthesia, and three more days later, the anti-DNP-AS antibody level in serum is measured. This measurement is made in the following way. 0.1 ml of blood collected from the rat tail vein is put into a test tube containing 0.2 ml of a heparin-added physiological saline and, after centrifugal separation at 3,000 r.p.m. at 4° C. for 15 minutes, the supernatant is collected to prepare 5-fold diluted serum, and the antibody level in the thus obtained serum is measured by making use of the passive cutaneous anaphylaxis reaction according to Tada et al method (Tada, T. and Okumura, K.: J. Immunol., 106 1002 (1971). The antibody level in serum is expressed by the maximum dilution of the sera exhibiting the blue spots of greater than 5 mm, and the antibody generation promoting activity (strength) of each preparation is expressed by units of activity, with the activity providing 1,024-times antibody level being indexed as 1,000 units. Specific activity is determined by dividing the unit strength by weight.

3. Insulin secretion promoting activity and immuno potentiating activity

The insulin secretion promoting active factor isolated and purified by the present inventors has not only the actions to promote insulin secretion of mammals and to maintain the blood sugar level within the normal range but also works marvelously for encouraging generation of antibodies and enhancing cellular immunity, and as this active factor produces these actions at an extremely small dose, it is highly useful as remedial or preventive medicines for divers diabetes or as medicinal preparations for treatment of the diseases resulting from abnormal immuno-function (such as malignant tumors, aplastic anemia, rheumatoid arthritis, etc.)

The present inventors have succeeded in separating this active factor having the said two effective activities into its constitutional materials, disclosing the fact that the pharmacological actions of these materials are distributed non-uniformly in the factor, and further succeeded in obtaining the novel single substances producing these two pharmacological activities individually by associating said constitutional materials.

The insulin secretion promoting active factor, its constitutiional elemental materials KS-I, KS-II and KS-III, and their associated substances KSA-I, KSA-II, KSA-III and KSA-IV, exhibit the insulin secretion promoting activity and immuno potentiating activity as measured by the abovesaid methods (Table 6).

The elemental materials of the active factor, when single, are weak in the insulin secretion promoting activity, but when associated with each other, they show strong activity. Particularly the associated substances including KS-III have strong insulin secretion promoting activity without exception, and hence it is considered that this component KS-III plays an important role in developing the insulin secretion promoting activity.

It is noted from these results that the insulin secretion promoting activity and the immuno potentiating activity are attributed to the different components, and they can be separated as different novel substances.

Table 6

|       | Insulin secretion promoting activity (units) | Immuno potentiating activity (units) |
|-------|----------------------------------------------|--------------------------------------|
| Dose  | 1 μg/rat                                     | 0.25 μg/rat                          |
| IAP   | 1290                                         | 4096                                 |
| Dose  | 10 μg/rat                                    | 10 μg/rat                            |
| KS-I  | 30                                           | 16                                   |
| KS-III| 159                                          | 16                                   |
| Dose  | 1 μg/rat                                     | 6 μg/rat                             |
| KSA-I | 1263                                         | —                                    |
| KSA-II| 1383                                         | 1024                                 |
| KSA-III| 1200                                        | 1024                                 |
| KSA-IV| 60                                           | 512                                  |

IAP: Insulin secretion promoting active factor

4. Side effects and toxicity

The insulin secretion promoting active factor isolated and purified by the present inventors produce a high insulin secretion promoting activity at an extremely small dose and is therefore credited with high availability as remedial and preventive medicines for various kinds of diabetes. It was found, however, that this active factor has some serious side effects such as increasing leukocyte count and histamine susceptivity. Strong antigenicity of this active factor was also noted. Particularly, such antigenicity is so strong that it might cause a serious result such as anaphylaxis shock on second and succeeding administrations. As this active factor takes its proper effects at an extremely small dose, the possibility of including such side effects in actual use is very slim, but it is of course highly desirable to get rid ot any side effect without affecting the proper activity of the substance for providing even safer and yet potent medicaments.

The present inventors found that the novel substances KSA-I, KSA-II, KSA-III and KSA-IV obtained by associating the once separated component materials of the active factor are markedly suppressed in side effects. Particularly, KSA-I, although substantially equal to the active factor in the insulin secretion promoting activity, is less than 1/50 in the action of increasing leukocyte count, less than 1/10 in the action of increasing histamine sensitivity and less than 1/30 in antigenicity as compared with the active factor. It was also confirmed that acute toxicity ($LD_{50}$) of the products from these novel substance is accordingly lessened.

Methods of determination of side effects

Determination of leukocytosis-inducing activity 0.2 ml of each specimen is injected into the tail vein of the ddy-strain female mice (5-week-old), and three days later, 20 μl of blood is collected from the tail vein. After diluting the collected blood 500 times with a physiological saline solution, the leukocyte count is measured by a microcell counter. The leukocytosis-promoting activity is given from the following formula:

$$\frac{\text{Leukocyte count increment in treated group}}{\text{Leukocyte count increment in control group}}$$

Literature:
Stephen I. Morse and Karen K. Baray: J. Exp. Med., 129, 523–550, 1969.

Determination of histamine-sensitizing activity 0.2 ml of each specimen is injected into the tail vein of groups of ddy-strain female mice (5-week-old, 6 rats a group), and three days later, 1 mg of histamine is administered intraperitoneally. Death and survival are checked one hour after histamine administration. The histamine-sensitizing activity is represented by the number of deaths.

Literature
Stephen I. Morse and Jaue H. Morse: J. Exp. Med., 143, 1483–1502, 1976.

Antigenicity

The specimen is administered three times a day to the groups of Hartley strain of male guinea pigs (weighing 250 gr, 6 guinea pigs a group), and 22 days after start of administration, 1 mg of the same specimen is injected intraveneously and the number of deaths caused by anaphylaxis shock is counted.

(1) Side effects of insulin secretion promoting active factor and KS-I, KS-II and KS-III:

The side effects of the insulin secretion promoting active factor and those of KS-I, KS-II and KS-III are shown in Table 7.

The insulin secretion promoting active factor shows histamine-sensitizing and leukocytosis-promoting activities as well as high antigenicity at an extremely small dose. The component materials KS-I, KS-II and KS-III of the active factor are generally more than 10 times lower in the degree of side effects than the active factor. Particularly, KS-I and KS-III are substantially free from such side effects. However, KS-II notably produces these side effects, and hence it is considered that this KS-II is mostly responsible for the strong side effects of the active factor.

(2) Side effects of KSA-I, KSA-II, KSA-III and KSA-IV:

The insulin secretion promoting activities and side effects of KSA-I, KSA-II, KSA-III and KSA-IV, which are the associated complexes of the component materials of the insulin secretion promoting active factor, are collectively shown in Table 8.

All of these associated substances, excluding KSA-IV, are almost same as the active factor in the insulin secretion prmoting activity, but any of these substances is markedly weakened in the leukocytosis-promoting activity. Amazingly, KSA-I shows no trace of such activity even if it is administered at a 10 times as high dose as the active factor. As regards sensitivity to histamine, KSA-I is lessened by approximately 50 times and KSA-II and KSA-III by 10 to 15 times, and as for antigenicity, KSA-I is lower than the active factor by more than 30 times and KSA-II and KSA-III about 5 times.

Thus, the associated substances are generally far weaker in side effects than the active factor, and particularly KSA-I produces no side effect even if it is administered at a 10 times greater dose. Such minimized side effect of KSA-I is probably due to absence of KS-II which is blamed for development of the side effects of the active factor.

(3) Toxicity

Acute toxicity levels ($LD_{50}$) (μg/kg body weight) of secretion promoting active factor, its components KS-I, KS-II and KS-III, and their associated substances KSA-I, KSA-II, KSA-III and KSA-IV are shown in Table 9.

Table 7

|   | LP activity | HS activity | ASA |
|---|---|---|---|
| Dose | 10 μg/mouse | 10 μg/mouse | 30 μg/guinea pig |
| KS-I | 1.5 | 0/6 | 0/6 |
| KS-II | 2.2 | 5/6 | 6/6 |
| KS-III | 0.9 | 0/6 | 2/6 |
| Dose | 1μg/mouse | 1 μg/mouse | 10 μg/guinea pig |
| IAP | 4.4 | 4/6 | 6/6 |

IAP: Insulin secretion promoting active factor
LP activity: Leukocytosis-promoting activity
HS activity: Histamine-sensitizing activity
ASA: Antigenicity Table 8

|   | IAP activity | LP activity | HS activity | ASA |
|---|---|---|---|---|
| Dose | 1 μg/rat | 10 μg/mouse | 10 μg/mouse | 50 μg/guinea pig |
| KSA-I | 1263 | 1.7 | 1/6 | 0/6 |
| KSA-II | 1383 | 3.4 | 6/6 | 6/6 |
| KSA-III | 1200 | 1.4 | 4/6 | 4/6 |
| KSA-IV | 60 | 1.2 | 2/6 | 5/6 |
| Dose | 1 μg/rat | 1 μg/mouse | 1μg/mouse | 10 μg/guinea pig |
| IAP | 1290 | 4.4 | 4/6 | 6/6 |

IAP: Insulin secretion promoting active factor
IAP activity: Insulin secretion promoting activity
LP activity: Leukocytosis-promoting activity
HS activity: Histamine-sensitizing activity
ASA: Antigenicity Table 9

|   | Subcutaneous | | Intravenous | |
|---|---|---|---|---|
|   | ♂ | ♀ | ♂ | ♀ |
| IAP | 540 | 580 | 220 | 155 |
| KS-I | 2500< | 2500< | 2500< | 2500< |
| KS-II | 1190 | 1025 | 750 | 860 |
| KS-III | 1950 | 1800 | 1325 | 1650 |
| KSA-I | 1520 | 1690 | 500 | 465 |
| KSA-II | 1250 | 1360 | 465 | 320 |
| KSA-III | 860 | 785 | 425 | 290 |
| KSA-IV | 1450 | 1675 | 515 | 505 |

IAP: Insuline secretion promoting active factor

5. Summary of pharmacological effects of respective activities

Summarized in the following are the pharmacological effects of the respective activities by taking as typical examples an associated substance KSA-I purified preparation obtained in Example III for evaluation of the insulin secretion promoting activity and an elemental material KS-II purified preparation obtained in Example II for evaluation of the immuno potentiating activity.

(A) Summary of pharmacological effects of insulin secretion promoting activity

KSA-I is particularly noted for its prominent insulin secretion promoting activity but it also has other pharmacologically used effects such as improvement of glucose tolerance, enhancement of insulin secretory response, promotion of healing of streptozotocin-induced diabetes and improvement of glucose tolerance of hereditary diabetes. Further, these activities sustain for several weeks to several months with a single administration of this substance. In view of the fact that the completely same phenomena were observed in the tested animals including mice, rats and dogs, it is considered that the pharmacological activities of this substance don't vary to any significant degree according to the difference in animal species.

It is considered that this substance finds its best application as a remedial medicine for diabetes. At present, medication for the diabetes depends on insulin injection or oral administration of antidiabetic drugs, but these are merely symptomatic treatments and, as things stand now, diabetes may be said an incurable disease. Further, the patient must go to hospital every day for insulin injections, and moreover, administration of the antidiabetic drugs involves the danger of causing abnormal decline of the blood sugar level. The outstanding advantage of this substance is that it not only has se a prominent insulin secretion promoting activity but it also has the action to increase the insulin concentration in the blood only when the blood sugar level has been elevated under various conditions (such as glucose loading in an elevated blood sugar level condition, such as during food ingestion) and to quickly return the elevated blood sugar value to the normal level. Another salient advantage of this substance is that its activity sustains for the period of several weeks to even several months with a single administration. Therefore, in case the insulin secretory reaction to the blood sugar level has declined, administration of this substance provokes normal insulin secretory activity. Thanks to these properties, this substance finds a wider scope of applications, that is, it is not only useful as a remedial medicine for diabetes, complications thereof and geriatric diseases originating from diabetes, but it also proves effective in application to the pre-diabetes-stage ailment or as a preventive, remedial or diagnostic medicine for the juvenile diabetes for which no effective curative means is yet available.

Shown in the following are some examples of animal experiments.

Insuline secretion promoting activity

The experimental conditions were same as used in measurement of activities described before, but in this experiment, the reactivity to the respective insulin secretion stimulants was measured on the third day after administration of the present active substance to rats and compared with the normal rats (control) (Table 10). In challenge of glucose which is the most physiological factor, a marked increase of insulin concentration in blood was seen over the control group notwithstanding the difference in course of glucose administration. A significant increase was also noted in reactivity to the hormone stimulants such as glucagon (1 mg/kg) and epinephrine (200 µg/kg). There was also observed elevated insulin secretory activity of tlubutamide (200 mg/kg) and glibenclamide (2 mg/kg) which are currently in use clinically as antidiabetic drugs. It was ascertained from these results that administration of the present active substance can markedly enhance the reactivity of the organism to the insulin secretion stimulants.

Table 11

Insulin secretion potentiation after administration of glucagon to dogs pretreated with the active substance

| Dose | | Time (min) after glucagon administration | |
|---|---|---|---|
| | | 0 | 5 |
| Control | | 11*1 | 2 |
| Treated groups | 50 U/kg | 13 | 53 |
| | 100 | 9 | 75 |
| | 500 | 12 | 183 |
| | 1000 | 18 | 365 |

Table 10

Promotion of reactivity to various insulin stimulants in rats (Wistar strain, male) pre-treated with the insulin secretion promoting active substance

| | | Control group | | | Treated group | | |
|---|---|---|---|---|---|---|---|
| | | Before administration ($\mu$U/ml)*1 | After administration ($\mu$U/ml) | Increment ($\mu$U) | Before administration | After administration | Increment |
| Glucose | Oral 0.5 g*2 | | | | | | |
| | 15*3 | 16 ± 1 | 102 ± 10 | 87 | 26 ± 8 | 308 ± 26 | 282 |
| | Intraperitoneal | | | | | | |
| | 0.3 g | 22 ± 3 | 125 ± 25 | 103 | 31 ± 3 | 525 ± 45 | 494 |
| | 15 | | | | | | |
| | Intravenous | | | | | | |
| | 0.05 g | | | | | | |
| | 15 | 25 ± 4 | 39 ± 8 | 14 | 28 ± 2 | 80 ± 3 | 52 |
| Glucagon | Intravenous | | | | | | |
| | 0.1 mg | 23 ± 1 | 45 ± 3 | 22 | 31 ± 4 | 96 ± 10 | 65 |
| | 5 | | | | | | |
| Epinephrine | Subcutaneous | | | | | | |
| | 20 µg | 19 ± 6 | 22 ± 2 | 3 | 30 ± 2 | 100 ± 18 | 70 |
| | 30 | | | | | | |
| | Oral 0.2 mg | | | | | | |
| | 60 | 28 ± 3 | 67 ± 5 | 39 | 41 ± 6 | 135 ± 8 | 94 |
| Tlubutamide | Intraperitoneal | | | | | | |
| | 20 mg | 25 ± 4 | 70 ± 4 | 45 | 38 ± 2 | 190 ± 16 | 152 |
| | 60 | | | | | | |

*1Insulin concentration in blood.
*2Dose/100 g body weight.
*3Blood collection time (min) after administration. The present active substance was injected (1,000 units) intravenously three days before the experiment. The figures show average values and standard errors in respective cases.

KSA-I was administered intravenously to dogs of beagle species, and 3 days later, glucagon (20 µg/kg body weight, intravenous injection) or glucose (0.3 g/kg body weight, intravenous injection) stimulation was made to examine the insulin secretion promoting activity. The test animals were fasted for 18 hours before the experiment.

The experimental results from glucagon stimulation are shown in Table 11. Promotion, though slight, of insulin secretion was noted over the control 5 minutes after glucagon administration at a dose of 50 U (as active substance)/kg (body weight), and insulin secretion was promoted proportionally to the increase of dose, reaching substantially the highest reaction at the dose of 1,000 U/kg. Similar potentiation of the insulin secretory activity was noticed in glucose (oral and intravenous administrations) and epinephrine challenges. These results indicate that noticeable enhancement of reactivity to the insulin secretion stimulants is induced in the dogs, too, by administration of the present active substance.

| | 2000 | 21 | 480 |
|---|---|---|---|

*1Mean value (µU/ml) of three cases

Glucose tolerance improving activity

Glucose was loaded orally to the rats of the same species as used previously, and attenuation of sugar level and insulin concentration in blood after glucose load were measured to determine glucose tolerance. In each test, glucose was given at a dose of 0.5 g/100 g body weight (rats) after 18- to 20-hour fast.

In the rats of the groups treated with the active substance, rise of glucose level in blood was markedly suppressed while there took place an evident increase of insulin concentration in blood, but the insulin concentration was quickly returned to the level before glucose loading in correspondence to normalization of blood sugar level, and no decline of blood sugar level due to excessive secretion of insulin was seen (Table 12). These results manifest marked improvement of glucose tolerance in the animals treated with the present active substance.

Table 12

Variations of blood sugar level and insulin concentration in blood after sugar load in rats

| Time (min) after glucose administration | 0 | 30 | 60 | 90 | 120 | 180 |
|---|---|---|---|---|---|---|
| Blood sugar level (mg/dl) | | | | | | |

Table 12-continued

Variations of blood sugar level and insulin concentration in blood after sugar load in rats

| Time (min) after glucose administration | 0 | 30 | 60 | 90 | 120 | 180 |
|---|---|---|---|---|---|---|
| Control group | 69 ± 3 | 135 ± 14 | 113 ± 8 | 109 ± 2 | 90 ± 2 | 88 ± 6 |
| Treated group | 63 ± 5 | 88 ± 6 | 85 ± 4 | 80 ± 3 | 77 ± 2 | 71 ± 5 |
| Insulin concentration ($\mu$U/ml) | | | | | | |
| Control group | 18 ± 3 | 32 ± 5 | 38 ± 6 | 29 ± 4 | 22 ± 3 | 24 ± 5 |
| Treated group | 21 ± 1 | 93 ± 6 | 51 ± 2 | 30 ± 5 | 31 ± 4 | 26 ± 5 |

The rats of the treated group were intravenously administered with the active substance (500 U) three days before start of the experiment.

Each figure shoes the average value of 5 cases±standard error.

Duration of activity

The pharmacological activities of the present active substance come to manifest themselves in several hours after administration, reach the highest levels in 3 to 7 days and then gradually decline. Shown below are the results of an experiment on duration of activities in rats (administered with the active substance at the dose of 500 units/rat).

The insulin secretory activity in rats was examined 1, 3, 7, 14, 21, 42 and 60 days after administration of the active substance. The results showed that a significantly high secretory activity is still maintained on the 42nd day after administration (Table 13).

It is judged from these results that the pharmacological activities of the present active substance sustain for several weeks to several months although the strength of such activities is uncertain for the reason of dosage.

Table 13

| Days after administration | Treated group (500 units/rat) | Control |
|---|---|---|
| 1 | 178 ± 16 | 68 ± 13 |
| 3 | 358 ± 29 | 75 ± 21 |
| 7 | 400 ± 58 | 69 ± 5 |
| 14 | 268 ± 19 | 71 ± 3 |
| 21 | 196 ± 32 | 80 ± 15 |
| 42 | 129 ± 40 | 65 ± 9 |
| 60 | 98 ± 12 | 77 ± 14 |

(Note)
Difference of insulin concentration in plasma ($\mu$U/ml) between 15 minutes after 30% glucose load and before such load (B) Summary on immuno potentiating activity 0.1 ml of Hanks' liquid containing 500 units of purified preparation of the sheet erythrocyte antibody potentiating active substance and $2 \times 10^8$ of red corpuscles was injected subcutaneously to the limb soles of C67B/6J mice who had been previously administered with purified KS-II preparation obtained in Example II, and 2 weeks later, blood was collected from the tail vein of the mice to obtain serum, and the erythrocyte flocculating antibody level in serum was measured. For measurement of antibody level, 0.1 ml of the solution prepared by diluting each serum specimen in multiples with a physiological saline solution was added with 0.01 ml of a 2% physiological saline solution of sheep erythrocyte, and after sufficient mixing and 2-hour incubation at 37° C., the condition of flocculation was observed, and the maximum multiple of dilution of the serum attended with flocculation was given as antibody level in serum. It was found as a result that the anti-sheet erythrocyte antibody level in serum in the case of immunization with sheep erythrocyte alone was only 64, whereas the antibody level in the case of immunization together with the purified preparation of the present active substance was 1,020, evidently indicating potentiating of antibody generation in the latter case. Thus, as the purified preparation of this substance shows a prominent adjuvant activity even for generation of antibody against sheep erythrocyte, it can be concluded that this substance is useful for treatment of various kinds of diseases resulting for abnormal immuno-functions.

(C)

As described in detail hereinabove, the novel substances according to this invention was very useful as remedial and preventive medicines for diabetes and as an ammunostabilizer. The effective dose for human applications varies depending on specific activity of the active substances. Usually, for use in solid forms for promotion of insulin secretory activity or immuno potentiating activity, they are administered within the amount range of 1 ng/kg (body weight) to several ten $\mu$g/kg (body weight).

As for the way of administration to the patient, intravenous injection is most effective in every use, but there may as well be employed other modes of administration such as intraperitoneal, intramuscular or subcutaneous injection, direct administration into the digestive organs, or oral, intrarectal, sublingual, nasal mucosa, intraarterial, intralymphangial or intratracheal administration.

As regards the form of administration, there may be cited injections, suppositories, enteric and gastric coatings, sublingual tablet and inhalants. A most simple example of injection compositions is a 1-ml mixture of 10,000 units of insulin secretory active substance, 9 mg of NaCl and sterile distilled water.

It will be apparent to those skilled in the art that other additives having no possibility of affecting the activity of the active substance may be suitably mixed in preparation of medicaments.

What is claimed is:

1. A protein fraction which is selected from the group consisting of KS-I, KS-II and KS-III which is prepared by the process of
culturing a pathogenic strain of *Bordetella pertussis,*
isolating from the cultured cells or culture medium a protein which has a molecular weight of 77,000±6,400 as determined by gel filtration and has insulin secretion promoting activity for a mammal, which protein in 0.1 M phosphate buffer (pH 7.0) is adsorbed on a hydroxyapatite column and eluted therefrom with 0.1 M phosphate buffer of pH 7.0 containing 0.5 M NaCl and which protein in SDS-polyacrylamide-gel electrophoresis, wherein an incubated mixture of 1% SDS, 1% mercaptoethanol and 4 M urea with 50 μg/tube of said protein is applied to 10% polyacrylamide-gel containing 1% SDS in 4-hour current application of 8 mA/gel, gives three main peptide-bands, mixing said protein into a solution of protein denaturant to dissociate it and recovering from the resultant mixture said protein fraction characterized by the following properties:

KS—I molecular weight: 63,000±5,200 as determined by gel filtration;
chemical composition: protein content as determined by the Lowry's method being ocer 97% by weight, the glucide content by the phenol-$H_2SO_4$ method being about 1% by weight and the lipid content being lower than the limit of detection,
the amino acids composition of the protein moiety: asparatic acid 8.1%; threonine 8.5%; serine 7.9%; glutamic acid 9.6%; proline 5.0%; glycine 10.0%; alanine 9.5%; cystine/2 1.1%; valine 6.2%; methionine 1.8%; isoleucine 4.5%; leucine 6.5%; tyrosine 7.6%; phenylalanine 2.8%; lysine 2.1%; histidine 1.6% and arginine 7.3%;
isoelectric pH value of 5.6±0.3, and
disc electrophoretic pattern, using acrylamide (polyacrylamide concentration, 7.5%; 1 N KOH-glacial acetic acid buffer (pH 4.3)) disc electrophoresis, giving a very sharp single band on the anode side;

KS—II molecular weight: 31,000±4,500 as determined by gel filtration;
chemical composition: protein content as determined by the Lowry method being over 95% by weight, the glucide content by the phenol-$H_2SO_4$ method being about 1% by weight and the lipid content being lower than the limit of detection;
the amino acid composition of the protein moiety: asparatic acid 9.3%; threonine 7.7%; serine 9.8%; glutamic acid 11.8%; proline 4.6%; glycine 9.8%; alanine 11.3%; cystine/2 N.D.; valine 7.4%; methionine 1.9%; isoleucine 4.0%; leucine 5.3%; tyrosine 6.2%; phenylalanine 2.5%; lysine 1.9%; histidine 1.1%; and arginine 5.4%;
isoelectric pH value of 5.4±0.4 and
disc electrophoretic pattern, using acrylamide (polyacrylamide concentration 7.5%; 1 N KOH-glacial acetic acid buffer (pH 4.3)) disc electrophoresis, giving a very sharp single band on the anode side;

KS—III molecular weight: 12,000±1,500 as determined by gel filtration,
chemical composition: protein content as determined by the Lowry method being over 96% by weight the glucide content by the phenol-$H_2SO_4$ method being about 1% by weight and the lipid content being lower than the limit of detection,
the amino acids composition of the protein moiety: asparatic acid 5.3; threonine 4.8%; serine 6.2%; glutamic acid 9.6%; proline 9.3%; glycine 8.1%; alanine 9.3%; cystine/2 2.3%; valine 10.2%; methionine 6.0%; isoleucine 2.2%; leucine 8.6%; tyrosine 2.5%; phenylalanine 4.5%; lysine 5.8%; histidine 0.5%; and arginine 4.8%;
isoelectric pH value of 8.3±0.3, and
disc electrophoretic pattern using acrylamide (polyacrylamide concentration 7.5%; 1 N KOH-glacial acetic acid buffer (pH 4.3)) disc electrophoresis, giving a very sharp single band on the cathode side.

2. A protein fraction KSA-I which is prepared by mixing KS-I with KS-III in a buffer solution to associate them and recovering therefrom, said protein fraction KSA-I which has the following properties:
molecular weight: 75,000±8,500 as determined by gel infiltration;
chemical composition: protein content as determined by the Lowry method being over 96% by weight, the glucide content by the phenol-$H_2SO_4$ method being about 1% by weight and the lipid content being lower than the limit of detection, and
isoelectric pH value of 6.8±0.4.

3. protein fraction KSA-II which is prepared by mixing KS-II with KS-III in a buffer solution to associate them and recovering therefrom, said protein fraction KSA-II which has the following properties:
molecular weight: 35,000±4,500 as determined by gel filtration,
chemical composition: protein content as determined by the Lowry method being over 96% by weight, the glucide content by the phenol-$H_2SO_4$ method being about 1% by weight and the lipid content being lower than the limit of detection, and
isoelectric pH value: of 6.3±0.3.

4. A protein fraction KSA-III which is prepared by mixing KS-I with KS-II and KS-III in a buffer solution to associate them and recovering therefrom said protein fraction KSA-III which has the following properties:
molecular weight: 85,000±13,000 as determined by gel filtration,
chemical composition: protein content as determined by the Lowry method being over 95% by weight, the glucide content by the phenol-$H_2SO_4$ method being about 1% by weight and the lipid content being lower than the limit of detection, and
isoelectric pH value of 8.2±0.5.

5. A protein fraction KSA-IV which is prepared by mixing KS-I with KS-II in a buffer solution and recovering therefrom said protein fraction KSA-IV which has the following properties:
molecular weight: 88,000±6,300 as determined by gel filtration,
chemical composition: protein content as determined by the Lowry method being over 95% by weight, the glucide content by the phenol-$H_2SO_4$ method being about 1% by weight and the lipid content being lower than the limit of detection, and
isoelectric pH value of 5.6±0.4.

6. A pharmaceutical composition for the treatment of prevention of diabetes which comprises an anti-diabetically effective amount of a protein fraction defined by any of claims 1 to 5 to promote insulin secretion, and a pharmaceutically acceptable carrier therefor.

7. A method of treating a patient suffering from diabetes which comprises administering to said patient an amount of a protein fraction defined by any of claims 1 to 5 capable of promoting insulin secretion in said patient.

8. The method of claim 7, wherein said protein fraction is KS-I.

9. The method of claim 7, wherein said protein fraction is KS-II.

10. The method of claim 7, wherein said protein fraction is KS-III.

11. The method of claim 7, wherein said protein fraction is KSA-I.

12. The method of claim 7, wherein said protein fraction is KSA-II.

13. The method of claim 7, wherein said protein fraction is KSA-III.

14. The method of claim 7, wherein said protein fraction is KSA-IV.

* * * * *